(12) United States Patent
Ciciarelli et al.

(10) Patent No.: US 10,307,598 B2
(45) Date of Patent: Jun. 4, 2019

(54) METHODS AND SYSTEMS FOR MANAGING SYNCHRONOUS CONDUCTED COMMUNICATION FOR AN IMPLANTABLE MEDICAL DEVICE

(71) Applicant: Pacesetter, Inc., Sunnyvale, CA (US)

(72) Inventors: Timothy Edward Ciciarelli, San Jose, CA (US); Benjamin T. Persson, Saratoga, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 294 days.

(21) Appl. No.: 15/215,466

(22) Filed: Jul. 20, 2016

(65) Prior Publication Data

US 2018/0021583 A1   Jan. 25, 2018

(51) Int. Cl.
| | | |
|---|---|---|
| A61N 1/365 | (2006.01) | |
| A61N 1/372 | (2006.01) | |
| A61N 1/37 | (2006.01) | |
| H04W 56/00 | (2009.01) | |
| A61N 1/375 | (2006.01) | |
| A61N 1/368 | (2006.01) | |

(52) U.S. Cl.
CPC ......... *A61N 1/36592* (2013.01); *A61N 1/368* (2013.01); *A61N 1/3684* (2013.01); *A61N 1/3727* (2013.01); *A61N 1/3756* (2013.01); *A61N 1/37205* (2013.01); *A61N 1/37217* (2013.01); *A61N 1/37288* (2013.01); *H04W 56/001* (2013.01)

(58) Field of Classification Search
CPC .......... A61N 1/00; A61N 1/365; A61N 1/368; A61N 1/375; A61N 1/37; A61N 1/372
USPC ....................................... 607/59, 18, 19, 17
See application file for complete search history.

(56) References Cited

U.S. PATENT DOCUMENTS

| | | | |
|---|---|---|---|
| 7,948,153 B1 | 5/2011 | Kellogg et al. | |
| 8,441,172 B2 | 5/2013 | Zhang | |
| 9,168,383 B2 | 10/2015 | Jacobson et al. | |
| 2007/0167993 A1* | 7/2007 | Dudding ............ | A61N 1/37276 607/59 |
| 2007/0293904 A1 | 12/2007 | Gelbart et al. | |
| 2010/0171394 A1 | 7/2010 | Glenn et al. | |
| 2012/0267982 A1 | 10/2012 | Carman et al. | |
| 2013/0226260 A1 | 8/2013 | Brenner et al. | |
| 2015/0365018 A1 | 12/2015 | Inman et al. | |
| 2016/0023000 A1* | 1/2016 | Cho ................... | A61N 1/36578 607/18 |

(Continued)

*Primary Examiner* — Carl H Layno
*Assistant Examiner* — Jon Eric C Morales
(74) *Attorney, Agent, or Firm* — Theresa A. Raymer

(57) ABSTRACT

Methods and systems are described for managing synchronous conducted communication for an implantable medical device (IMD). The IMD further comprises electrodes and sensing circuitry. The sensing circuitry is configured to detect physiologic events. A receiver amplifier is coupled to the electrodes. The receiver amplifier is configured to receive conducted communications signals via the electrodes. A controller is configured to establish synchronous conducted communication with a transmit device. The controller includes a receive window timing (RWT) module configured to manage an on-off cycle of the receiver amplifier based on first and second receive window timing schemes. The RWT module switches between the first and second receive window timing schemes based on a condition of the synchronous conducted communication.

17 Claims, 8 Drawing Sheets

(56) References Cited

U.S. PATENT DOCUMENTS

2016/0121129 A1   5/2016  Persson et al.
2016/0144190 A1*  5/2016  Cao .................... A61N 1/36514
                                                              607/17

* cited by examiner

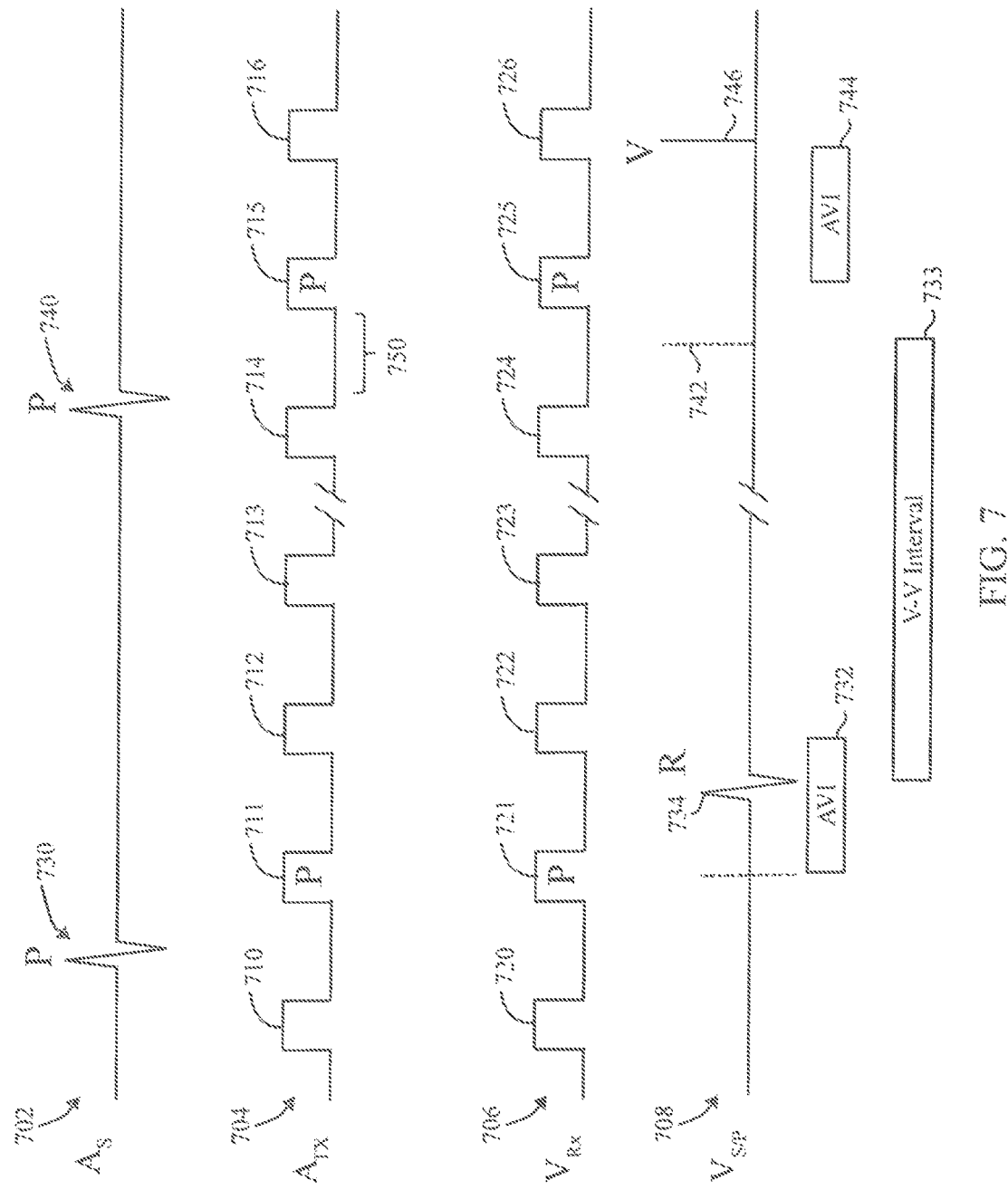

METHODS AND SYSTEMS FOR MANAGING SYNCHRONOUS CONDUCTED COMMUNICATION FOR AN IMPLANTABLE MEDICAL DEVICE

BACKGROUND OF THE INVENTION

Embodiments herein generally relate to implantable medical devices, and more particularly to synchronous conducted communication with an implantable medical device.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Known pulse generators can include various sensors for estimating metabolic demand, to enable an increase in pacing rate proportional and appropriate for the level of exercise. The function is usually known as rate-responsive pacing. For example, an accelerometer can measure body motion and indicate activity level. A pressure transducer in the heart can sense the timing between opening and closing of various cardiac valves, or can give a measure of intracardiac pressure directly, both of which change with changing stroke volume. Stroke volume increases with increased activity level. A temperature sensor can detect changes in a patient's blood temperature, which varies based on activity level. The pacemaker can increase rate proportional to a detected increase in activity.

Pulse generator parameters are usually interrogated and modified by a programming device outside the body, via a loosely coupled transformer with one inductance within the body and another outside, or via electromagnetic radiation with one antenna within the body and another outside.

Leadless implantable medical devices (LIMDs) have been proposed such as in U.S. Pat. No. 9,168,383, titled "LEADLESS CARDIAC PACEMAKER WITH CONDUCTED COMMUNICATION" issuing Oct. 27, 2015, the complete subject matter of which is incorporated herein by reference. In general, in one aspect, a leadless pacemaker for pacing a heart of a human includes a hermetic housing and at least two electrodes on or near the hermetic housing. The electrodes are configured to deliver energy to stimulate the heart and to transfer information, through conducted communication, to or from a separate device. The separate device can be a second leadless pacemaker, a defibriliator, a conventional pacemaker, an implanted programmer, or a programmer external to the body of the human. The conducted communication information can be encoded in sub-threshold pulses. The LIMD can further include a pulse generator in the housing, and the pulse generator can be configured to provide energy to the electrodes for various therapies (e.g., stimulate the heart, stimulate nerve tissue, etc.). The LIMD further includes a controller that is configured to communicate with the external device by transferring the information through the electrodes. The controller can communicate with the external device by transferring the information through the electrodes either i) during a pacing pulse or ii) during a refractory period.

However, it is desirable to provide alternative solutions for establishing conducted communication with an LIMD. For example, existing conducted communication strategies may utilize asynchronous communications timing between the LIMD and the separate device (e.g., another LIMD, programmer, etc.). The communications are asynchronous as neither device knows when the other device is going to begin to transmit information.

It has been proposed to implant LIMDs in multiple chambers of the heart and to coordinate operation therebetween to provide the functionality of a dual chamber pacemaker. A dual chamber pacemaker performs pacing and sensing in two chambers of the heart. One LIMD is resident in one chamber and one LIMD is resident in another chamber with no wires connected there between. For example, when one device is in the ventricle and one is in the atrium, the ventricular device needs to know when an atrial paced or sensed event occurred so the device can appropriately time when to deliver or inhibit ventricular pacing. To support dual chamber functionality utilizing at least two LIMDs, implant to implant communication is maintained with each of the LIMD conveying local activity information to the other LIMD. For example, an atrial LIMD would inform a ventricular LIMD each time that an atrial sensed or paced event occurred. Similarly, the ventricular LIMD would inform the atrial LIMD each time that a ventricular sensed or paced event occurred.

The LIMD includes a conducted communications circuit that includes, among other things, a data receiver amplifier that is coupled to the electrodes and "listens" for incoming communications when the receiver amplifier is active. The receiver amplifier utilizes a certain amount of power when active and thus, draws upon the battery when active. It may not be desirable to leave the data receiver amplifier of the LIMO in an active state 100% of the time because the current draw may become unacceptable and reduce the life of the battery.

One proposed solution, as described in U.S. Published Patent Application No. 2016/0121129, filed May 5, 2016, and titled "SYSTEM AND METHOD FOR LOW POWER COMMUNICATION BETWEEN IMPLANTABLE DEVICES", is to use a very low current wakeup-receiver that remains on all the time without drawing a significant portion of current from the battery. Low frequency wake up pulses are transmitted from one LIMD and are received by an always-on low-frequency, low-power wake-up amplifier of another LIMD. The receiving LIMD responds to the low frequency wake up pulses by temporarily turning on a high-frequency, higher-power data receiver amplifier that is used to receive data from the transmitting LIMD. However, the foregoing solution experiences certain limits. First, an always-on low-power low-frequency wake-up amplifier may demand excessive current in order to satisfy sensitivity targets in certain applications. Second, the wake-Lip transmission pulse waveform may have a high enough current/voltage amplitude or low enough frequency content to stimulate tissue. Tissue stimulation due to communication guises is undesirable because it could cause stimulation when oversensing T-waves or when the pacemaker is set to a pacing off mode. If, to reduce the chance of tissue stimulation, the wake-up pulse waveform's current/voltage amplitude is lowered or frequency is increased the always-on wake-up receiver will need to be made more sensitive at a cost of increased power consumption.

A need remains for improved methods and systems that provide low power, non-stimulating transmit/receive communications schemes for implantable medical devices.

SUMMARY

In accordance with embodiments herein, an implantable medical device is provided comprising a housing that is configured to be implanted entirely within a first region of a patient. The implantable medical device further comprises electrodes and sensing circuitry coupled to the electrodes. The sensing circuitry is configured to detect physiologic events occurring in the first region. A receiver amplifier is coupled to the electrodes.

The receiver amplifier is configured to receive conducted communications signals through the electrodes. A controller is configured to establish synchronous conducted communication with a transmit device. The controller includes a receive window timing (RWT) module configured to manage an on-off cycle of the receiver amplifier based on first and second receive window timing schemes. The RWT module switches between the first and second receive window timing schemes based on a condition of the synchronous conducted communication.

Optionally, the RWT module may switch between first and second receive window timing schemes that utilizes first and second receive windows, respectively, having different durations. Before the synchronous conducted communication is established, the RWT module may be configured to switch to the first receive window timing scheme in which a persistent active receive window may be maintained. After the synchronous conducted communication is established, the RWT module may be configured to switch to the second receive window timing scheme that comprises a series of successive receive windows separated by in-active intervals. The receive windows have a duration that may be substantially less than a duration of the inactive intervals.

Optionally, the controller may be configured to perform a calibration operation that maintains the second receive window timing scheme calibrated with a transmit window timing scheme of the transmit device. The controller may perform the calibration operation by modifying the second receive window timing scheme by shifting at least one of i) a reference point defining a timing of the receive windows, ii) a duration of the receive windows or iii) a window-to-window interval based on information received from the transmit device. The controller may perform the calibration operation by shifting a reference point defining a timing of the receive windows based on the timing difference. The controller may be configured to analyze the physiologic events and, based thereon, manage the pulse generator to deliver a therapy in the local tissue of interest.

In accordance with embodiments herein, a method is described for providing synchronous conducted communication for an implantable medical device (IMD). The method comprises providing an IMD that has a housing configured to be implanted entirely within a first region of a patient. The IMD includes a controller, sensing circuitry, a receiver amplifier coupled to electrodes. The method utilizes the electrodes to sense conducted communications electrodes from a transmitting device, utilizes the electrodes to detect physiologic events occurring in the first region and utilizes a receiver amplifier to receive conducted communications signals via the electrodes. The method establishes synchronous conducted communication with a transmit device, manages an on-off cycle of the receiver amplifier based on first and second receive window timing schemes and switches between the first and second receive window timing schemes based on a condition of the synchronous conducted communication.

Optionally, the method may further define the second receive window timing scheme to correspond to a transmit window timing scheme utilized by the transmit device. The second receive window timing scheme and the transmit window timing scheme may comprise corresponding series of successive receive and transmit windows, respectively, that are temporarily aligned with one another. The first receive window timing scheme may be utilized before the synchronous conducted communication is established. The first receive window timing scheme may maintain a persistent active receive window.

Optionally, the method may further comprise switching to the second receive window timing scheme after the synchronous conducted communication is established. The second receive window timing scheme may comprise a series of successive receive windows separated by in-active intervals. The method may define the second receive window timing scheme to include receive windows having a duty cycle of no more than 50% of a period of the second receive window timing scheme (e.g., 0.01% to 50%). The duty cycle may represent a percentage of the period in which the receive windows are active. The method may perform a calibration operation that maintains the second receive window timing scheme calibrated with a transmit window timing scheme of the transmit device. Further, the method may modify the second receive window timing scheme by increasing a duration of the receive window as a function of time relative to a point in time when synchronous conducted communication was established. The calibration operation may be performed based on at least one of manufacturing information or information received from the transmit device.

In accordance with embodiments herein, a method is provided, comprising configuring first and second leadless implantable medical devices (LIMDS) to operate cooperatively in a DDD pacemaker mode. Each of the LIMDs includes a housing, electrodes, receive amplifier, sensing circuitry and a controller. The first and second LIMDs are configured to be implanted entirely within first and second chambers of the heart, respectively. The method detects at least one of paced or sensed events at the first LIMD at an event detection rate. The method defines a transmit window timing scheme for the first LIMD and a receive window timing scheme for the second LIMD. The transmit and receive window timing schemes include transmit and receive windows temporarily aligned with one another. The transmit and receive windows are spaced apart by a window-to-window interval in accordance with a transmit rate. The transmit rate is independent of and differs from, the sensed event detection rate (which is dependent on physiologic activity and is asynchronous to the LIMD logic). When a paced or sensed event is detected at the first LIMD, the first LIMD transmits event related information in a next successive transmit window, through conducted communication. The method receives the event related information at the second LIMD during a receive window overlapping the next successive transmit window and manages delivery of pacing pulses at the second LIMD based on the event related information received from the first LIMD.

Optionally, the managing operation may comprise initiating an interval timer, at the second LIMD, based on the event related information received from the first LIMD, and may deliver pacing pulses at the second LIMD when the interval timer expires before detection of an intrinsic event by the second LIMD. The first LIMD may transmit the event related information after a delay that occurs from detection of the paced or sensed event and the next successive transmit window. Optionally, the method may further comprise performing selective transmission at the first LIMD, in which paced or sensed event activity is included only in a subset of the transmit windows.

Optionally, the managing operation may comprise initiating an event interval timer at the second LIMD. When the event interval timer expires, the second LIMD suspends delivering of pacing pulses at the second LIMD until after a next successive receive window at the second LIMD following the expiration of the event interval timer.

BRIEF DESCRIPTION OF THE DRAWINGS

FIG. 7 illustrates a timing diagram in connection with managing cooperative operation between IMDs that exhibit a certain level of communication granularity in accordance with embodiments herein.

DETAILED DESCRIPTION

Figure 1A:
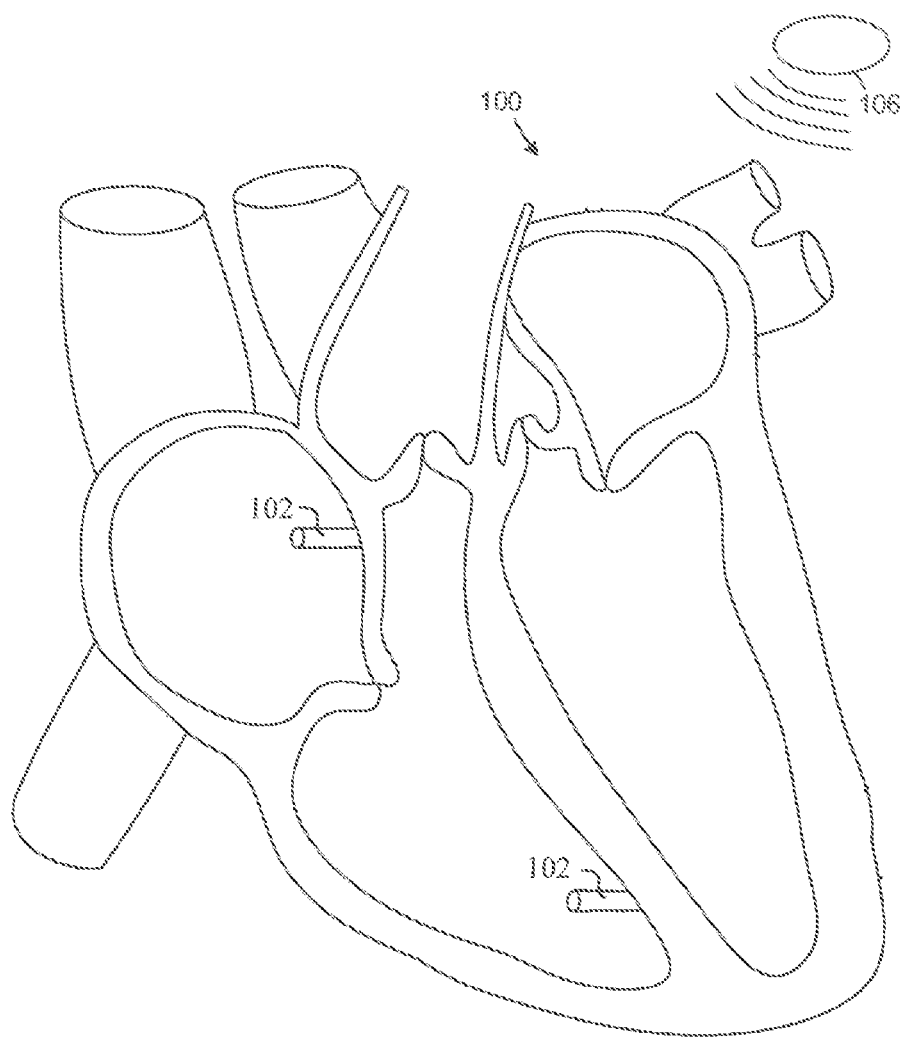
FIG. 1A illustrates a pictorial view depicting an embodiment of an implantable system that may be utilized to deliver various types of therapy and/or monitor physiologic conditions in accordance with embodiments herein.

FIG. 1A illustrates a pictorial view depicting an embodiment of an implantable system 100 that may be utilized to deliver various types of therapy and/or monitor physiologic conditions in accordance with embodiments herein. The system 100 comprises one or more implantable medical devices (IMD) 102. As described further below, the IMD 102 comprises a housing, multiple electrodes coupled to the housing, and a pulse generator hermetically contained within the housing and electrically coupled to the electrodes. The pulse generator may be configured for sourcing energy internal to the housing, generating and delivering electrical pulses to the electrodes. A controller can also be hermetically contained within the housing as part of the pulse generator and communicatively coupled to the electrodes. The controller can control, among other things, recording of physiologic characteristics of interest and/or electrical pulse delivery based on the sensed activity.

In the example of FIG. 1A, a pair of IMDs 102 are illustrated to be located in different first and second chambers of the heart. For example, one IMD 102 is located in the right atrium, while a second IMD 102 is located in the right ventricle. The MDs 102 coordinate the operation therebetween based in part on information conveyed between the IMDs 102 during operation. The information conveyed between the IMDs 102 may include, among other things, physiologic data regarding activity occurring in the corresponding local chamber. For example, the atrial IMD 102 may perform sensing and pacing operations in the right atrium, while the ventricular IMD 102 may perform sensing and pacing operations in the right ventricle. The physiologic data conveyed between the atrial and ventricular IMDs 102 includes, among other things, the detection of sensed intrinsic local events (e.g., sensed atrial events or sensed ventricular events). The physiologic data also includes paced local events (e.g. paced atrial events or paced ventricular events). Additionally or alternatively, the information conveyed between the atrial and ventricular IMDs 102 may include device related information, such as synchronization information, oscillator clock timing information, battery status, quality information regarding received signals and the like. Additionally or alternatively, the physiologic data may include other information.

While the IMDs 102 are located in the right atrium and ventricle, optionally, the IMDs 102 may be located in other chamber combinations of the heart, as well as outside of the heart. Optionally, the IMDs 102 may be located in a blood pod without directly engaging local tissue. Optionally, the IMDs 102 may be implemented eddy to perform monitoring operations, without delivery of therapy. For example, an IMD 102 may be a cardiac monitoring device that is located outside of, but in relative close proximity to, the heart. As another example, one or more IMDs 102 may represent a subcutaneous implantable device located in a subcutaneous pocket and configured to perform monitoring and/or deliver therapy. As another example, one or more IMDs 102 may be configured to perform neural stimulation. The IMD 102 is boated proximate to nerve tissue of interest (e.g., along the spinal column, dorsal root, brainstem, within the brain, etc.). The IMD 102 may be configured to perform monitoring of neural activity, without delivering neural stimulation. Optionally, the IMD 102 may not require tissue contact to monitor and/or deliver therapy. For example, blood pressure may be measured with or without direct tissue contact.

In the example of FIG. 1A, the IMDs 102 represent leadless devices in which the electrodes are located directly on the housing of the device, without a lead extending from the device housing. Optionally, the IMDs 102 may be implemented with leads, where the conducted communication occurs between one or more electrodes on the lead and/or on the housing. Examples of other IMDs that may be configured to implement the conducted communication embodiments described herein are described in U.S. Pat. No. 9,168,383, issued Oct. 27, 2015, and titled "LEADLESS CARDIAC PACEMAKER WITH CONDUCTED COM- MUNICATION," the complete subject matter of which is incorporated by reference in its entirety.

Figure 1B:
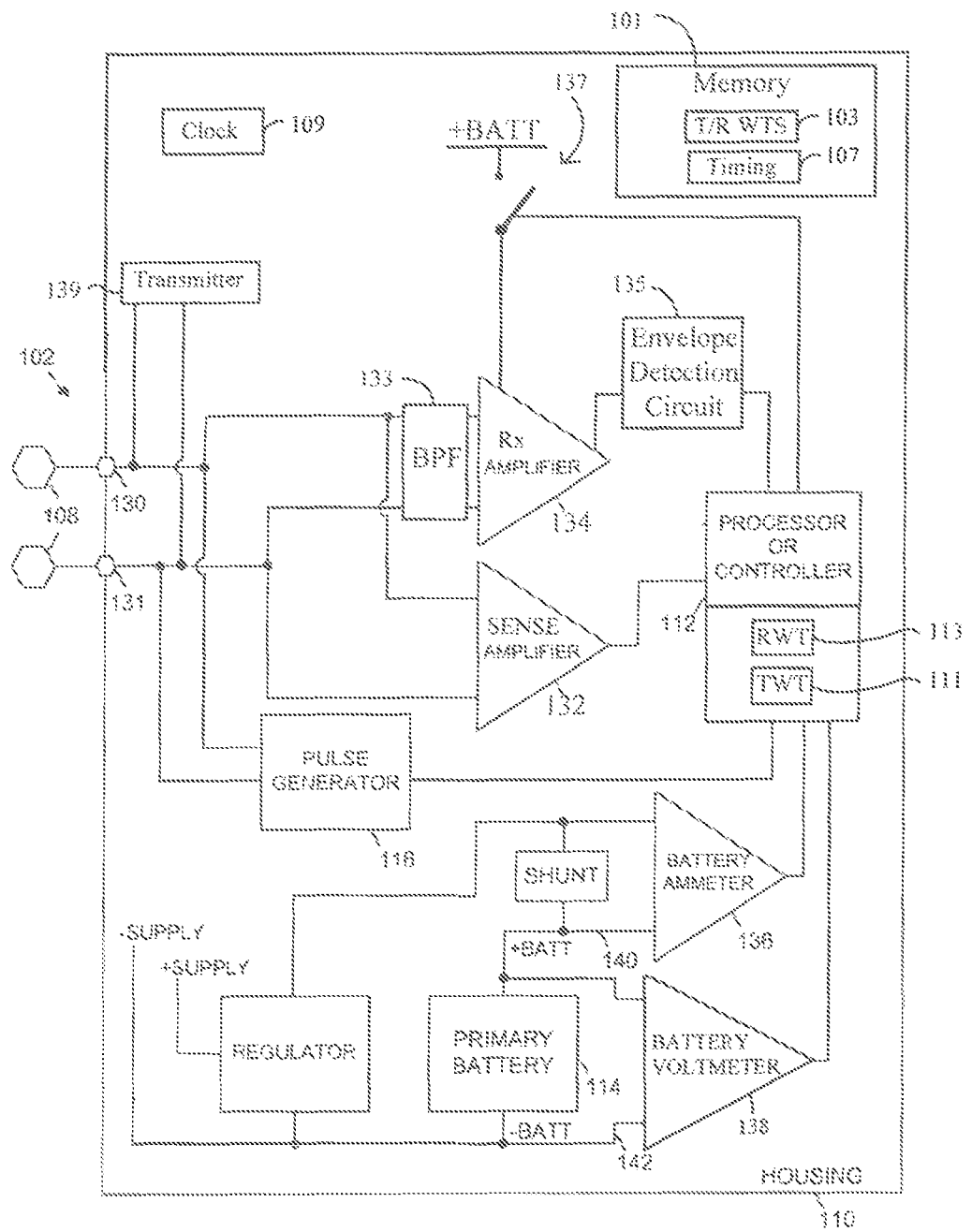
FIG. 1B illustrates a block diagram of at least a portion of the elements enclosed in an IMD in accordance with an embodiment herein.

FIG. 1B illustrates a block diagram of at least a portion of the elements enclosed in an IMD 102 in accordance with an embodiment herein. The IMD 102 has at least two electrodes 108 located within, on, or near the housing 110, for delivering pacing pulses to, and sensing electrical activity from, the cardiac chamber, and for bidirectional communication with at least one other device within or outside the body. In some arrangements, the electrodes 108 can be formed integrally to an outer surface of the housing 110. Hermetic feedthroughs 130, 131 conduct electrode signals through the housing 110. The housing 110 contains a battery 114 to provide power for pacing, sensing, and communication. In certain embodiments battery 114 is a primary battery. For example, in certain embodiments, battery 14 is a lithium carbon monofluoride (Li/CFx) battery. In alternative embodiments, battery 14 is a secondary rechargeable battery. In certain embodiments, an energy harvester is electrically connected to a charging circuit within the IMD 102 to recharge the battery 14. In certain embodiments, energy harvested using an energy harvester is stored in a capacitor. In certain embodiments, energy harvested using an energy harvester is used in real time. In certain embodiments, an energy harvester is used in lieu of battery 14. The energy harvester may use piezoelectric elements that convert mechanical stress, strain, vibration, or bending into an electrical potential. U.S. Pat. Nos. 8,441,172 and 7,948,153 and U.S. Pub. Nos. 2013/0226260, 2010/0171394, 2012/0267982, 2015/0365018, and 2007/0293904, each of which is incorporated herein by reference, describe energy harvester systems and methods that may be used in accordance with the current disclosure.

The IMD 102 contains sensing circuits 132 for sensing cardiac activity from the electrodes 108. The IMD 102 includes one or more docks 109 that generate timing signals used by the controller 112 and other components in the IMD 102 to maintain synchronous operation. As explained herein, transmit and receive window timing schemes are maintained based on the timing signals from the clock 109.

The IMD 102 includes a communications receiver amplifier 134 for receiving communications information from other devices via the electrodes 108. The receiver amplifier 134 is switched between active and in-active states by opening and closing a switch 137 that is connected to the battery power supply. The conducted communications receiver amplifier 134 is switched to the active state to initiate a receive window and is switched to an in-active state to terminate the receive window.

A processor or controller circuit 112 is provided to control the operations discussed herein as well as other conventional operations. A pulse generator 116 generates stimulation pulses (e.g., pacing pulses, defibrillation pulses, nerve tissue stimulation pulses) for delivery via the electrodes 108. The pulse generator 116 is also controlled by the controller 112 to transmit conducted communications information during transmit windows via conducted communication to at least one other device via the electrodes 108. The controller 112 determines when synchronous conducted communication has been established with a transmit IMD or other transmit device. Synchronous conducted communication may occur in various manners. For example, the controller 112 may determine that synchronous conducted communication occurs each time that the controller of a receive IMD detects a conducted communication from a transmit IMD or other transmit device. Optionally, the controller 112 may determine that synchronous conducted communication does not occur until the controller 112 of the receive IMD collects conducted communication information related to the transmit timing of a transmit IMD or device. For example, the information related to transmit timing may represent a reference marker, transmit clock timing related information and the like.

The IMD 102 further contains circuits for monitoring device health (e.g., a battery current monitor 136 and a battery voltage monitor 138).

The pulse generator 116 is configured to generate and deliver electrical pulses to the electrodes 108 powered from a source 112 contained entirely within the housing 110. An activity sensor (not shown) can be hermetically contained within the housing 110 and adapted to sense activity. The controller 112 may include one or more processor, central processing unit, state machine, programmable logic array, and the like. The controller 112 is hermetically contained within the housing 110 and communicatively coupled to the pulse generator 116 and the electrodes 108. In some embodiments, the controller 112 is configured to control electrical pulse delivery at least partly based on the sensed activity.

In some embodiments, the controller 112 can be a processor that controls electrical pulse delivery and/or application of the activity sensor according to one or more programmable parameters with the processor programmable by communication signals transmitted via the electrodes 108. The IMD 102 includes memory 101 that may store software and/or firmware that is executed by the controller 112 to perform operations described herein. The memory 101 may also store device status related data, patient physiologic information and the like. For example, the memory 101 may store information related to paced and/or sensed events, as well as flags and interval timers utilized in connection with managing pacemaker and other device related operations (e.g., AV interval, VA interval, blanking periods, refractory periods, etc.). The memory 101 also stores transmit/receive window timing schemes 103, such as the transmit window timing schemes and receive window timing schemes described herein (e.g., FIGS. 4A, 4B and 7). The memory 101 stores timing information 107 that used to shift the transmit and receive window timing schemes relative to a reference point. For example, as explained herein, the receive window timing scheme may be calibrated periodically or otherwise shifted. When the receive window timing scheme is calibrated or shifted, the timing information 107 is updated. The calibration operation may be performed based on at least one of manufacturing information or information received from a transmit device.

Figure 4A:
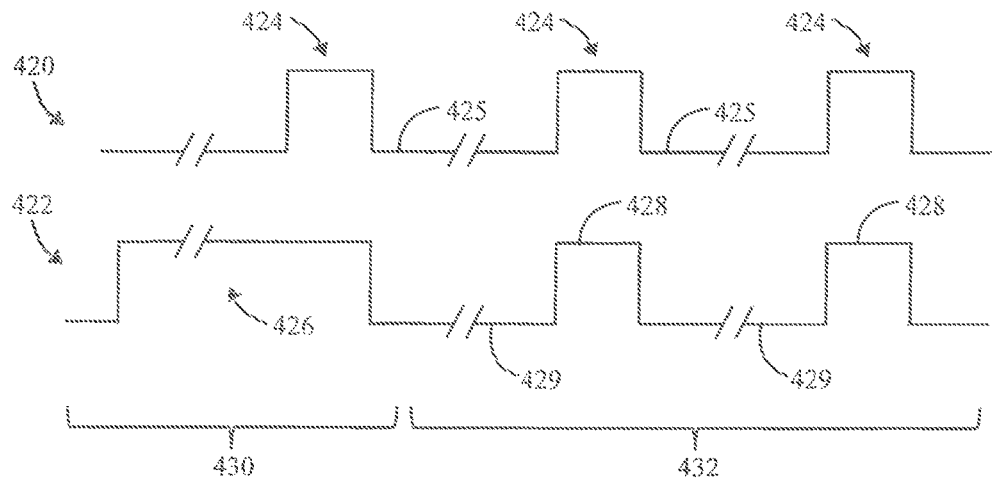
FIG. 4A illustrates transmit/receive window timing schemes implemented in accordance with an embodiment herein.
Figure 4B:
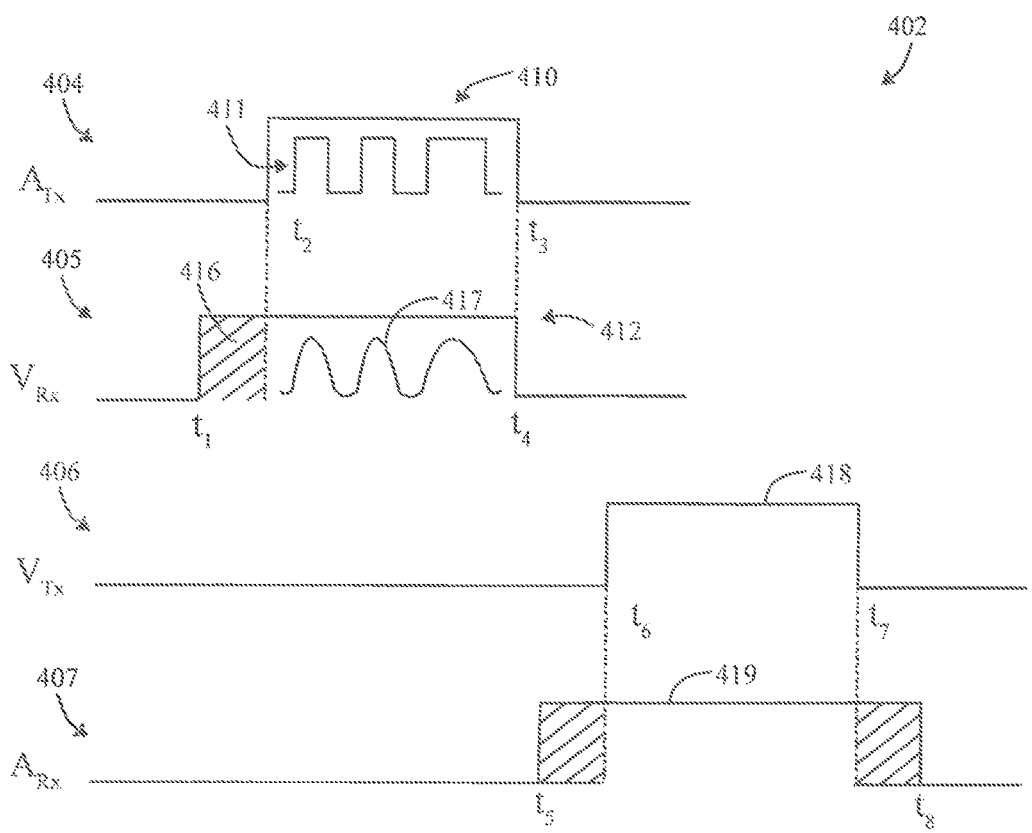
FIG. 4B illustrates a transmit/receive window timing scheme for synchronous bi-directional communication between a pair of IMDs, positioned in an atrium and a ventricle, in accordance with embodiments herein.

The IMD 102 includes one or more transmitters 139 that are controlled by the controller 112 to generate and transmit conducted communications information over the electrodes 108 (e.g., see the communications pulses 411 in FIG. 4B). The controller 112 includes a transmit window timing module 111 that manages the interval and duration of transmit windows utilized by the transmitter 139. The transmit window timing module 111 utilizes a one or more predetermined transmit window timing scheme as described herein. By way of example only, transmit window timing schemes are illustrated and described in connection with FIGS. 4A and 7.

The controller 112 including a receive window timing (RWT) module 113 that is configured to open and close the switch 137 to manage an on-off cycle of the receiver amplifier based on a receive window timing scheme. More specifically, the RWT module 113 cycles the receiver amplifier between an on/active state and an off/in-active state as defined by the receive window timing scheme. For example, a window timing scheme may be defined by a series of state changes (e.g. on/off state of switch 137) with predetermined durations (e.g. clock cycles) there between, where the series of state changes and predetermined durations are repeated on a periodic basis. The RWT module 113 switches between at least first and second receive window timing schemes (described below in more detail) based on a condition of the synchronous conducted communication. For example, the condition may indicate whether synchronous conducted communication has occurred within a predetermined trailing time period. Before synchronous conducted communication is established (or when synchronous conducted communication is not established within the predetermined trailing time period), the RWT module 113 is configured to switch to the first receive window timing scheme in which a persistent active receive window is maintained. After the synchronous conducted communication is established and during the predetermined trailing time period), the RWT module 113 utilizes the second receive window timing scheme that comprises a series of successive receive windows separated by in-active intervals. As described herein, the receive windows are generally managed to have a duration that is substantially less than a duration of the in-active intervals. For example, the receive windows may be active for a window duration of 100 μs, with 64 active receive windows per second, resulting in a duty cycle of 0.0064. It is recognized that numerous other receive window configurations may be utilized.

The term "duty cycle" is used to refer to an amount or percentage of one time period in which a component or channel (e.g., a receive amplifier or receive channel) is active. For example, a series of receive windows may be separated by in-active intervals such that the receive windows are active for less than 5.0% of the period. As another example, the series of receive windows may be separated by in-active intervals such that the receive windows are active for less 1.0% of the period (e.g., 0.64%).

Optionally, multiple receive window timing schemes may be used after synchronous conducted communication is achieved.

In accordance with embodiments herein, the controller 112 may direct the RWT module 113 to modify the second receive window timing scheme by shifting at least one of i) a reference point defining a start time of the receive windows, ii) a duration of the receive windows or iii) a window-to-window interval, based on information received from the transmit device. The information may include a transmit clock timing, a reference marker in a message and the like. Additionally or alternatively, the information may represent data that the transmit IMD intends to send, or the information may represent data obtained by the receive IMD from measuring characteristics of the transmit signal. The information is used to calculate a timing difference. For example, the RWT module 113 may modify the second receive window timing scheme by shifting the reference point (defining the timing of the receive windows) based on the timing difference. Additionally or alternatively, the RWT module 113 may modify the second receive window timing scheme by increasing the duration of the receive window as a function of time relative to a point in time when the synchronous conducted communication was established. Various alternative and additional operations of the RWT module 113 are discussed herein.

Also shown in FIG. 1B, the primary battery 114 has positive terminal 140 and negative terminal 142. The amplifier or amplifiers 132, 134 are configured to amplify signals received from the electrodes 108 and to detect cardiac contractions, and further can receive information from the external device or devices 106. One or both of the amplifiers 132, 134 may include a bandpass filter 133 upstream thereof to filter the incoming signals. An envelope detection circuit 135 may be provided downstream of the receiver amplifier 134. The envelope detection circuit 135 is configured to identify rising and falling edges of communication pulses. The pulse edges are detected when the amplitude of the communications signal crosses upper and/or lower thresholds. In response thereto, the envelope detection circuit 135 outputs a pulse sequence corresponding to the communications signal. The pulse sequence may comprise a series of pulses that shifts between zero, a high positive state, a low positive state, and one or more other predetermined intermediate states. The controller 112 analyzes the pulse sequence to detect predetermined pulse patterns. One unique pulse pattern is indicative of a beginning of a conducted communications signal. Various pulse patterns are defined to convey information, such as physiologic or device related data (e.g., paced event, sensed event, low battery).

Figure 2:
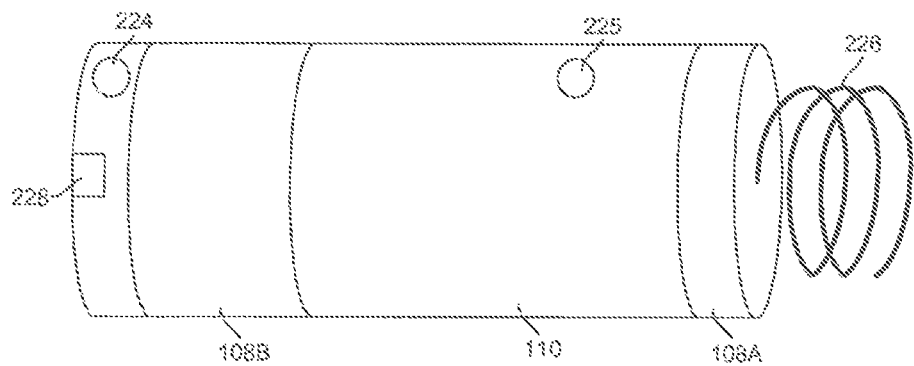
FIG. 2 illustrates examples of structures for attaching the housing to the interior or exterior wall of cardiac muscle in accordance with embodiments herein.

FIG. 2 illustrates examples of structures for attaching the housing 110 to the interior or exterior wall of cardiac muscle. A helix 226 and slot 228 may be provided to enable insertion of the device endocardially or epicardially through a guiding catheter. A screwdriver stylet can be used to rotate the housing 110 and force the helix 226 into muscle, thus affixing the electrode 108A in contact with stimulable tissue. Electrode 108B can serve as an indifferent electrode for sensing and pacing. The helix 226 may be coated for electrical insulation, and a steroid-eluting matrix may be included near the helix to minimize fibrotic reaction, as is known in conventional pacing electrode-leads.

In other configurations, suture holes 224 and 225 can be used to affix the device directly to cardiac muscle with ligatures during procedures where the exterior surface of the heart can be accessed. Other attachment structures used with conventional cardiac electrode-leads including tines or barbs for grasping trabeculae in the interior of the ventricle, atrium, or coronary sinus may also be used in conjunction with or instead of the illustrative attachment structures.

Figure 3:
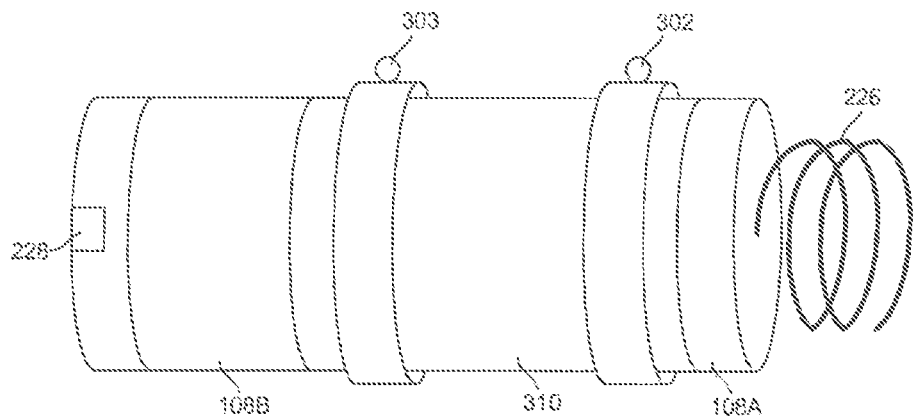
FIG. 3 illustrates a pictorial view of an embodiment of a pulse generator that includes a cylindrical metal housing with an annular electrode and a second electrode in accordance with embodiments herein.

FIG. 3 illustrates a pictorial view of an embodiment of a pulse generator that includes a cylindrical metal housing 310 with an annular electrode 108A and a second electrode 108B. Housing 310 can be constructed from titanium or stainless steel. Electrode 108A can be constructed using a platinum or platinum-iridium wire and a ceramic or glass feed-thru to provide electrical isolation from the metal housing. The housing 310 can be coated with a biocompatible polymer such as medical grade silicone or polyurethane except for the region outlined by electrode 108B. The distance between electrodes 108A and 108B should be selected to optimize sensing amplitudes and pacing thresholds. The helix 226 and slot 228 can be used for insertion of the device endocardially or epicardially through a guiding catheter. In addition, suture sleeves 302 and 303 made from silicone can be used to affix to the device directly to cardiac muscle with ligatures.

FIG. 4A illustrates transmit/receive window timing schemes implemented in accordance with an embodiment herein. A transmit channel 420 is associated with a first IMD and a receive channel 422 is associated with a second IMD. The transmit channel 420 includes a synchronous series of transmit windows 424, during which information is conductively transmitted from the first IMD (transmit IMD). The receive channel 422, associated with the second IMD (receive IMD), is managed by the receive window timing module 113 (FIG. 1B) to switch between first and second receive window timing schemes based on a condition of the synchronous conducted communication (e.g., whether synchronous conducted communication has been established).

Before synchronous conducted communication is established, the RWT module 113 of the receive IMD is configured to maintain a first receive window timing scheme 430 which includes a persistent active receive window 426. The RWT module 113 maintains the receive window 426 in an active state for an extended period of time, longer than a normal receive window, such as until synchronous conducted communication is achieved between the transmit and receive IMDs. The receive window 426 is generally active all or most of the pre-synchronization receive window timing scheme 430. Optionally, the receive window 426 may be active only for select portions of the pre-synchronization receive window timing scheme 430.

The interval including receive window 426 represents the first or pre-synchronous receive window timing scheme 430, while the interval thereafter represents a second or post synchronous receive window timing scheme 432. The RWT module 113 changes between the pre-synchronization and post synchronization receive window timing schemes 430, 432 based on whether synchronous conducted communication occurs at the receiving IMD during a predetermined trailing time period. For example, even after synchronous conducted communication is achieved, synchronization may be lost for various reasons. When synchronous conducted communication does not occur for the predetermined trailing time period, the RWT module 113 of the receive IMD switches back to the pre-synchronization receive window timing scheme 430.

Once synchronous conducted communication is achieved between the transmitting and receiving IMDs, the receive IMD switches to the receive window timing scheme 432 which comprises a series of successive receive windows 428 that are separated by inactive intervals 429. The receive windows 428 are spaced a predetermined distance from one another and remain active for predetermined window durations that are shorter than the receive window 428. The receive windows 428 and in-active intervals 429 have durations and window-to-window intervals that correspond to and temporally align with the duration and window-to-window interval of transmit windows 424 and in-active intervals 425. For example, the transmit and receive windows 424, 428 may be temporary aligned to start (e.g., have leading edges that occur at the same point in time). The transmit and receive windows 424, 428 may be aligned to end (e.g. have trailing edges that also occur at the same point in time). The transmit and receive window timing schemes are defined such that the receive windows 428 entirely or at least partially overlap the transmit windows 424. For example, the receive windows 428 may be defined to start before the corresponding transmit windows 424. As another example, the receive windows 428 may be defined to end after the corresponding transmit windows 424. In addition, the transmit and receive window timing schemes are defined to have equal or substantially similar window-to-window intervals such that the in-active intervals 425, 429 are substantially the same in length and overlap.

The in-active intervals 429 may have a common duration for all in-active intervals 429. Alternatively, the duration of the in-active intervals 429 may differ from one another. Additionally or alternatively, groups of receive windows 428 may be defined such that receive windows 428 within a first group are separated by a first in-active interval 429 with a first duration, while the receive windows 428 within a second group are separated by an in-active interval 429 having a different second duration.

It is understood that IMDs will generally (but not always) maintain bi-directional communication with one another. FIG. 4A illustrates a single transmit channel and a single receive channel. Optionally, multiple transmit channels and/or multiple receive channels may be used.

FIG. 4B illustrates a transmit/receive window timing scheme 402 for synchronous bi-directional communication between two or more IMDs, positioned in an atrium and a ventricle, in accordance with embodiments herein. FIG. 4B illustrates amplifier control signals 404-407 that are supplied to the transmitters and receive amplifiers in the first/atrial and second/ventricular IMDs 102. More specifically, amplifier control signals 404 and 406 are supplied to the transmitters for the atrial and ventricular IMDs, respectively. The amplifier control signals 405, 407 are supplied to the receive amplifiers for the ventricular and atrial IMDs, respectively. The control signal 405 for the receive amplifier in the ventricular IMD maintains an in-active state until time $t_1$ and then switches to an active state unto time $t_4$. While in the active state between times $t_1$ and $t_4$, the control signal 405 defines an active receive window 412, during which the ventricular IMD listens for conducted communications. The control signal 404 for the transmitter in the atrial IMD maintains an in-active state until time $t_2$ and then switches to an active state until time $t_3$. While in the active state between times $t_2$ and $t_3$, the control signal 404 defines an active transmit window 410, during which the atrial IMD conductively transmits information.

Within the active transmit window 410, conducted communications pulses 411 are transmitted. The conducted communications pulses 411 may be defined in accordance with various protocols. For example, the conducted communications pulses 411 may follow an on-off keying (OOK) protocol. A conducted communications message may be within a single transmit window or distributed over a series of transmit windows. The conductive communications message may include various message sections, such as a header section, a data section and the like. As one example, the conducted communications message starts with a transmit key, such as an OOK bit pattern indicating the beginning of a message transmission (e.g., 00110101, 0101, 00110011, etc.).

A receive IMD listens during the receive window 412 and collects analog signals 417 that are detected by the receive amplifier 134 (FIG. 1B). The signals 417 sensed over the communications receive channel (during the receive window 412) are processed by the envelope detection circuit 135 to form a pulse pattern based on threshold crossings by the signal 417. The pulse pattern is analyzed by the controller 112 in search of the transmit key indicating the beginning of a message transmission. When the transmit key is identified, the receive IMD processes information collected during one or more receive windows in accordance with the predetermined format and protocol.

FIG. 4B illustrates one example of the manner in which the transmit and receive windows 410, 412 are managed to align with one another based on predefined transmit/receive window timing schemes 103 stored in the memory of the corresponding IMD. In the example of FIG. 4B, the control signal 404 is scheduled to activate the receive amplifier shortly before initiation of the transmit window 410. The difference in time between the beginnings of the transmit and receive windows 410, 412 may correspond to an amplifier warm-up period 416, during which the receive amplifier becomes active, and prepares to identify and process incoming conducted communications. By time $t_2$, the receive amplifier is operating in a steady state to sense signals received at the electrodes in search of incoming signals that satisfy the criteria for conducted communication information. Optionally, the warm-up period 416 may be omitted and the transmit and receive windows 410 and 412 initiated and terminated at the same time.

Optionally, the control signals 406 and 407 may manage the timing relation between a transmit window 418 of the ventricular IMD and a receive window 419 at the atrial IMD in an alternative manner. The transmit window 418 is activated at the time $t_6$ and deactivated at time $t_7$. The receive window 419 is activated at time $t_5$ and deactivated at time $t_8$. For example, the timing relation may be managed to account for clock drift in either direction which may result in the transmit window 418 beginning before or after a beginning of the receive window 419. As one option, the transmit and receive windows 418, 419 are managed to activate the receive window 419 at the time $t_5$ which occurs before the transmit window 418 is activated at time $t_6$. In addition, the time $t_8$ (deactivation of the receive window 419) lags time $t_7$ (deactivation of the transmit window 418) such that the receive window 419 has a greater duration than the duration of the transmit window 418. For example, it may be desirable to define the receive window 419 to be longer than the transmit window 418 to allow for timing drift between the timing clocks used by the atrial and ventricular IMDs.

In accordance with embodiments herein, methods and systems are provided herein that maintain the receive window active for a portion of the overall duty cycle such that the receiver amplifiers are off some of the time. By maintaining the receiver amplifier in-active, an average current draw is limited as compared to solutions that maintain the receiver amplifiers active all or a majority of the time. For example, when the receiver amplifier is only active for a receive window of 100 us, if the receive window is repeated 64 times each second, then the duty cycle is 0.0064 (64*0.0001), or 0.64%. Continuing the example, when the receive amplifier exhibits a nominal current draw of 50 uA, the average current draw during a single receive window would be reduced to 320 nA. By way of example, the receive windows 412 may have a duration of between approximately 1.6 us and 7.8 ms. As another example, the duration of the receive windows 412 may be defined as a percentage of the complete period between the start of successive receive windows. For example, the receive windows 412 may be set to have equal duration and be active between 50% and 0.01% of the overall period (15.625 ms in this example).

Following implant, the IMDs are turned on and perform an initial synchronization. However, throughout operation, synchronization may be lost for various reasons. Accordingly, as explained herein, the IMDs restore synchronization when lost. In accordance with embodiments herein, in order to achieve synchronization, one or both of the IMD track the timing scheme(s) of the other IMD(s). For example, one IMD may track a transmit/receive reference marker that is maintained by the other IMD. In the event either IMD detects a loss of synchronization, the receive IMD switches back to the first/pre-synchronization window timing scheme (430 in FIG. 4A). When synchronization is not restored, the IMD enters a backup independent mode (e.g., pacing mode) that does not require communication between the IMDs.

Figure 5:
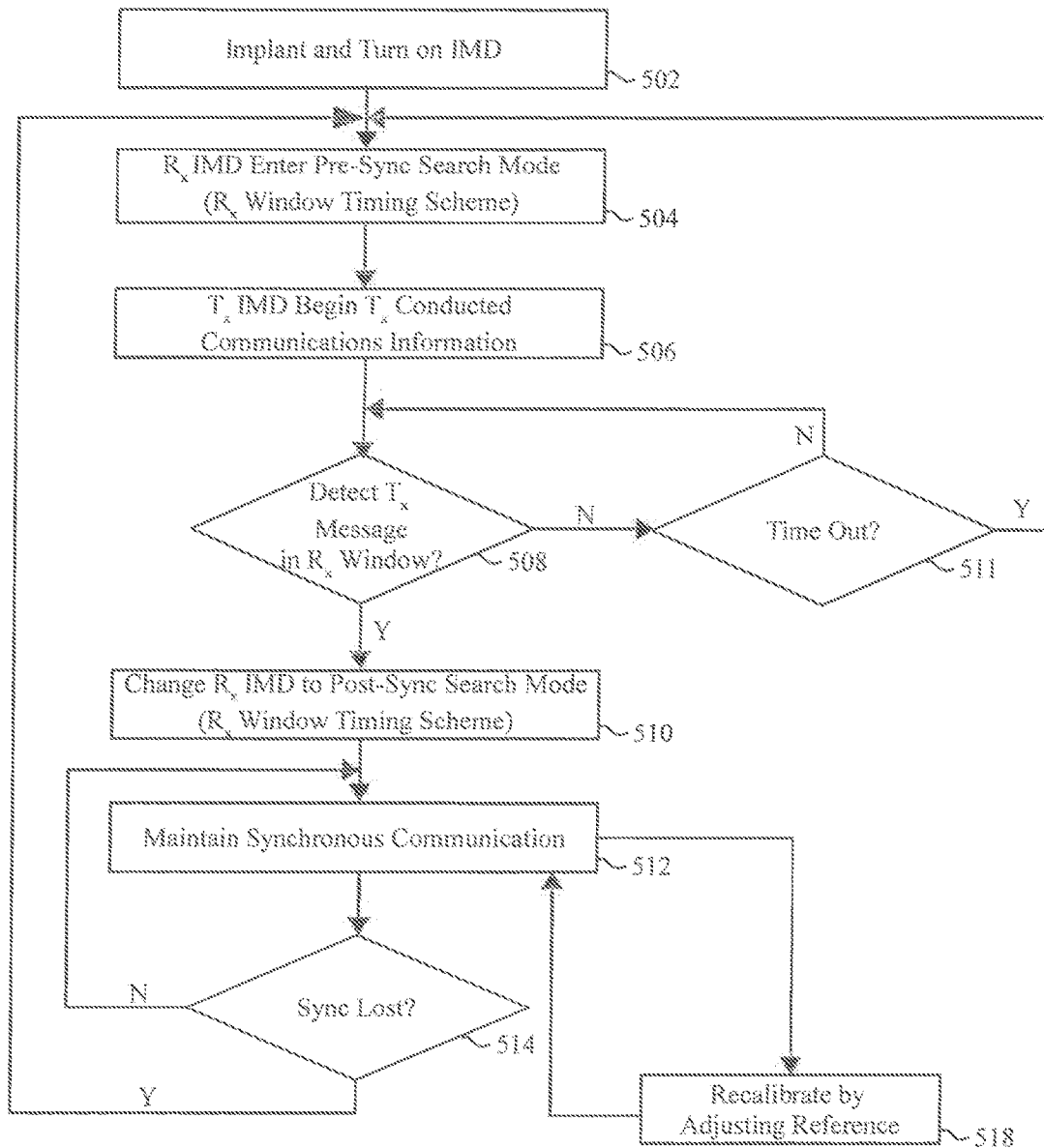
FIG. 5 illustrates a flow chart for establishing and maintaining conducted communications between an IMD and another device in accordance with embodiments herein.

FIG. 5 illustrates a flow chart for establishing and maintaining conducted communications between an IMD and another device, such as another IMD, an external device, etc. The operations of FIG. 6 are described from the perspective of a "first" or receive IMD. However, the operations of FIG. 5 may be performed by multiple IMDs. The operations of FIG. 5 also refer to a second or transmit IMD, which may represent any other device (implanted or external to the patient). By way of example, the operations of FIG. 5 related to the first or receive IMD may be carried out by an atrial IMD, while the operations of the second or transmit IMD are carried out by a ventricular IMD. Additionally, or alternatively, the receive and transmit IMD may be reversed (e.g., the ventricular IMD is the receive IMD and the atrial IMD is the transmit IMD). As another option, the receive IMD may represent an atrial or ventricular IMD, while the transmit device represents a cardiac monitor device, a subcutaneous IMD, a neurostimulation device, an external device that is not implanted within the patient and the like.

At 502, a receive IMD is implanted at a select location. The IMD may be positioned proximate to local tissue of interest, in a blood pool or elsewhere. For example, the IMD may be implanted in or near a chamber of the heart, at or near nerve tissue of interest, in a subcutaneous pocket, or at another location suitable to perform monitoring of one or more physiologic characteristics of interest. At 502, the IMD is turned on, or otherwise instructed to begin to transmit and receive conducted communications information.

At 504, the receive IMD enters a pre-synchronization search mode, in which a receive amplifier is maintained active for one or more persistent periods of time in accordance with a first receive window timing scheme. At 506, the transmit IMD begins to transmit information. During the pre-synchronization search mode, the receive amplifier may be maintained in a constantly active state. Alternatively, the receive amplifier may be maintained in an active state for extended periods of time, separated by short intervals of inactivity. Optionally, the receive amplifier may be maintained in an active state for extended periods of time, separated by in-active states, but where the active states are of different duration. For example, during the pre-synchronization search mode, an initial receive window may be continuous for all or a substantial majority of a search period. The extended receive window may be used for a select number of search periods, in the event that a transmit event is not detected (and synchronization is not achieved) during the select number of search periods, the receive window may be adjusted to be shorter or longer for a second number of search periods. In the event that a transmit event is still not detected, the search mode may be continued or terminated, pending a determination of the reason that synchronization was not achieved.

The nature of the information transmitted by the transmit IMD may represent simple identification information and/or more detailed or complex information. For example, the information may include physiologic data and/or markers identifying the occurrence of a paced and/or sensed event. The information may include other physiologic data such as the AV delay. Additionally or alternatively, the information may include device identification and device operational information.

At 508, the processor of the receive IMD determines whether a valid communication has been received from the transmit IMD. If no valid communications (transmit message) are received during the current pre-synchronization search mode, flow returns to 511. At 511, the processor determines whether a time out period has expired. When the time out period has not expired, flow returns to 508 and the receive IMD again waits for a valid communication. The receive IMD may remain in the loop at 508 for a select period of time before adjusting the search mode (e.g., change the search window). When the time out period expires, flow returns to 504. Optionally, the loop at 508 may be terminated by a command.

At 508, when a valid communication is received, flow moves to 510. At 510, the controller of the receive IMD changes the search mode to a post-synchronization search mode. As described herein, the post-synchronization search mode utilizes a receive window timing scheme (e.g., 432 in FIG. 4A) that has shorter receive windows as compared to a length of the receive window used during the pre-synchronization search mode.

At 512, the receive IMO and the transmit IMD establish synchronous conducted communication. During synchronous conducted communication, the receive IMD receives valid communications from the transmit IMD. For example, the receive IMD may determine that synchronous conducted communication exists when the receive IMD receives a valid communications packet from the transmit IMD during one out of a select number of receive windows. Additionally or alternatively, the receive IMD may determine that synchronous conducted communication is maintained when the receive IMD receives information indicating the presence of a sensed or paced event every cardiac cycle or once out of a select number of cardiac cycles. As another example, the transmit IMD may periodically transmit a "keep alive" message which maintains synchronous conducted communication. Additional or alternative criteria may be utilized to define whether synchronous conducted communication is maintained.

At 514, the controller of the receive IMD determines whether synchronous conducted communication has been maintained or lost, if synchronization has been maintained, flow returns to 512. If synchronization is lost, flow returns to 504.

In addition, at 512 flow may branch to 518 when it is desirable to perform a calibration operation. Calibration may be performed while synchronous communication is being maintained. Additionally or alternatively, calibration may be performed as part of 510 when synchronization is first achieved. At 512, the controller of the receive IMD determines whether to perform a calibration operation. If the receive IMD is to be recalibrated, flow moves to 518. When it is determined to perform calibration, at 518, the processor of the receive IMD performs a recalibration operation which is described below in more detail in connection with FIGS. 6A and 6B. Flow then returns from 518 to 512, where synchronous communication is maintained.

Communications Link Maintenance

As explained herein, in accordance with various embodiments, one way for transmit and receive IMDs to synchronize transmit and receive windows is to keep the receiver amplifier(s) of the receive ND on until conducted communication is detected from the transmit IMD. For example, one of the transmit and/or receive IMDs may be designated as a master IMD which never has to synchronize the corresponding transmit or receive window. By way of example, an atrial IMD may be designated as a master IMD, while the ventricular IMD is designated as a slave IMD. The slave IMD would maintain the receive amplifier on all the time until a conducted communications pulse is received from the master IMD. The atrial IMD will represent a transmit IMD in connection with transmitting atrial sensed/paced event related information and represent a receive IMD in connection with receiving ventricular sensed/paced event related information. Similarly, the ventricular IMD will represent a transmit IMD in connection with transmitting ventricular sensed/paced event related information and represent a receive IMD in connection with receiving atrial sensed/paced event related information.

It is recognized that an IMD represents a transmit IMD in connection with information being transmitted from the IMD, while the same IMD represents a receive IMD in connection with information being received at the IMD. Various embodiments have been described herein in connection with establishing synchronization between a receive IMD and a transmit IMD. Once synchronization is established, the receive and transmit IMDs manage receive and transmit windows, respectively, (e.g. 424 and 428 in FIG. 4A) in accordance with predetermined transmit and receive timing schemes. For example, each receive window may be defined to have a predetermined window duration, with the start times of successive receive windows separated by a predetermined window-to-window interval. The window duration and window-to-window interval may be defined based on a time elapsed since a reference point/marker or other criteria. Each IMD includes one or more docks that generate clock reference signals that are utilized by one or more processors, controllers, circuits, pulse generators and the like within the IMD. The window duration and window-to-window Interval may be defined relative to select numbers of clock cycles. For example, the window duration may be set to correspond to a desired number of clock cycles. As another example, the window-to-window interval may be set to correspond to a desired number of clock cycles, where the first receive window follows a reference marker/point by a desired number of clock cycles.

The window duration and window-to-window interval may vary in an unknown or uncontrolled manner over time due to practical limitations of circuit operations and clock characteristics. For example, the clocks of the IMDs may experience drift or changes in the timing or duration of clock cycles. Accordingly, an individual IMD may only Maintain a desired transmit/receive timing scheme within a relative tolerance of the clock and other circuits therein.

Over time the communication (transmit and receive) windows will drift apart, relative to one another, unless the relative timing of the IMDs are periodically maintained or calibrated. For example, even if it is assumed that the docks for a pair of transmit and receive IMDs are substantially the same, the more time that passes since the last synchronization, the more the communication (transmit and receive) windows will drift apart. For instance, if one clock is 10 Hz faster than the other, after passage of 1 second, the communication windows will shift, relative to one another, by 10 clock cycles. Stated another way, the transmit and receive windows grow out of synch by 10 cycles with the passage of each second. Various embodiments are described herein for maintaining a select timing relation between transmit and receive IMDs.

Figure 6A:
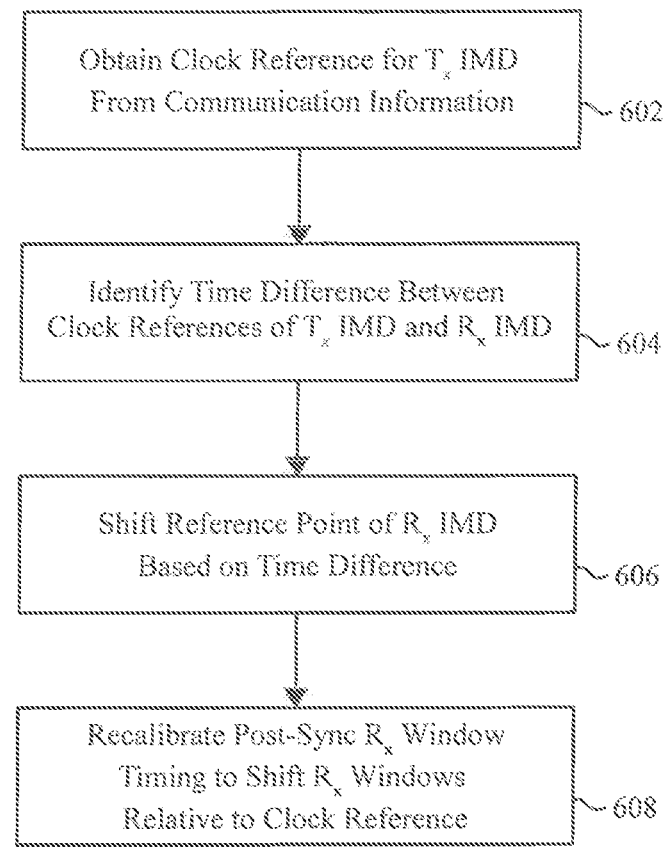
FIG. 6A illustrates a method for performing a timing calibration operation in accordance with an embodiment herein.

FIG. 6A illustrates a method for performing a timing calibration operation in accordance with an embodiment herein. The method of FIG. 6A may be implemented by one or more controllers in one or more IMDs to maintain a known timing relation between the IMDs. For example, the calibration operation of FIG. 6A may be performed by a designated IMD from a set of IMDs. Additionally or alternatively, the calibration operation maybe performed by all IMDs that perform receive operations. The calibration operation calibrates a frequency delta between the clocks of the transmit and receive MDs to maintain a duration of the receive windows substantially the same as, or within a desired tolerance of, the duration of the transmit windows. The controllers of the MDs are configured to identify a difference between transmit and receive window timing based on incoming conducted communication. The controller shifts the receive window timing based on a difference between the transmit timing of the incoming conducted communication and the receive window timing. In general, the calibration enables the IMDs to substantially align the beginnings (leading edges) of transmit and receive windows, and to substantially align the endings (trailing edges) of transmit and receive windows. The calibration operation of FIG. 6A may be performed periodically or randomly. Additionally or alternatively, the calibration operation may be performed in connection with each received message and/or after a set number of receive messages. Additionally or alternatively, the calibration operation may be performed in response to particular criteria, such as during excessive periods of patient activity, during extended periods of paced events and the like.

At 602, the controller of the receive ND monitors conducted communications from the transmit IMD for a reference marker related to calibration information. For example, the reference marker may represent a clock reference or marker that is conveyed during a conducted communication signal/packet from a transmit IMD. At 604, the controller identifies a time difference between the clock reference within the incoming conducted communication from the transmit IMD and a clock reference of the receive IMD. For example, the controller may determine that the clock references of the transmit and receive IMDs have drifted by a number of clock cycles relative to one another (e.g., one-half clock cycle, three-quarters of a clock cycle, 5 clock cycles, 10 clock cycles, etc.). As one example, a drift may occur by a fractional clock cycle when the IMDs transmit with a divided version of a reference clock and use either a reference clock (or a less divided frequency version of that same clock) for received signal sampling.

At 606, the controller of the receive IMD shifts the reference point that defines a timing of the receive windows utilized by the receive IMD. The reference point is shifted based on the time difference determined at 604. For example, when the time difference between the clock references is determined to be five clock cycles, the reference point is shifted five clock cycles in connection there with. The direction in which the reference point is shifted is dependent upon whether the clock reference of the receive IMD leads or lags the clock reference of the transmit IMD. For example, when it is determined that the clock reference for the receive IMD lags behind (has drifted backward) the clock reference for the transmit IMD, at 606, the reference point is shifted backward in time by a corresponding number of clock cycles. Alternatively, when it is determined that the clock reference of the receive IMD leads (has drifted forward) the clock reference of the transmit IMD, at 606, the reference point is shifted forward in time by a corresponding number of clock cycles. For example, the timing information 107 stored in memory 101 (FIG. 1B) may be updated to shift the reference point backward or forward.

At 608, the controller of the receive IMD re-calibrates the post synchronization receive window timing to shift the receive windows relative to the clock reference. Thereafter, receive windows are opened and closed based on the recalibrated receive window timing. Optionally, the calibration operation may be omitted entirely or combined with additional techniques for tracking a timing relation between different IMDs.

Figure 6B:
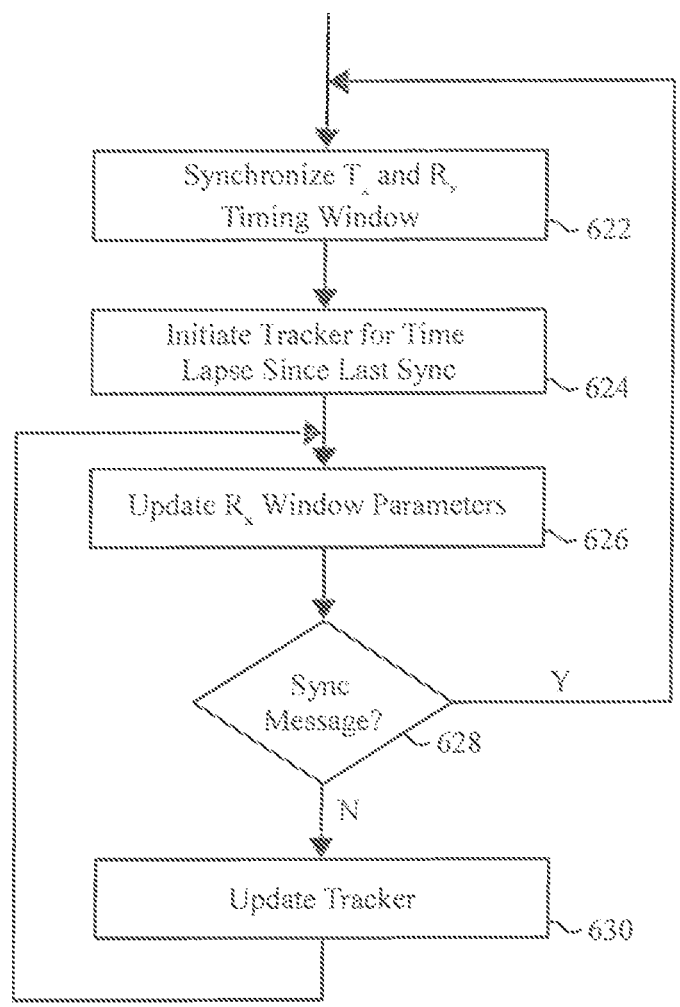
FIG. 6B illustrates a method for performing a timing adjustment operation in accordance with embodiments herein.

FIG. 6B illustrates a method for performing a timing adjustment operation in accordance with embodiments herein. The method of FIG. 6B may be implemented by one or more processors in one or more IMDs. For example, the operation of FIG. 6B may be performed by a designated IMD from a set of IMDs. Additionally or alternatively, the operations maybe performed by all IMDs that perform receive operations. At 622, the controller of the receive IMD may perform a synchronization operation to synchronize the transmit and receive windows of corresponding transmit and receive IMDs. The operation at 622 may be performed at the time of implant, or any time thereafter. For example, periodically, the transmit and receive IMDs may perform a timing synchronization operation to reset the beginning of transmit and receive windows relative to one another in a desired manner. Alternatively, the operation at 622 may be performed with the intervention of an external programmer that uses timing calibration parameters such as those measured at the time, of manufacture and stored in memory.

At 624, the controller of the receive IMD initiates a tracker (e.g. a timer) to track the time lapse that has occurred since the last time that the transmit and receive IMDs were synchronized. At 626, the controller of the receive IMD updates the receive window parameters based on the time lapse since the last timing synchronization operation. At 624, the controller determines whether a new timing synchronization message has been received from the transmit IMD. When a synchronization message is received, flow returns to 622. Otherwise, flow continues to 630. At 630, the tracker is updated to extend the time lapse since the last timing synchronization operation. Thereafter, flow returns to 626 where the receive window parameters are updated.

The operations of FIG. 6B are continuously repeated such that, as the time lapse extends from the last timing synchronization operation, the receive window parameters are correspondingly updated. For example, the controller may update the receive window parameters by extending the length of the receive window as the tracker extends the duration of the time lapse. Additionally or alternatively, the controller may update the receive window parameters by extending the receive window-to-window interval as the time lapse extends since the last timing synchronization operation, pow in accordance with the embodiment of FIG. 6B, the controller of the receive IMD tracks a duration of time that has lapsed since a last synchronization operation between the transmit and receive IMDs. As the duration of time increases, the controller adjusts (increases) the duration of the receive windows to increase the duration of the receiver "on time" as a function of time since the last synchronization. By continuously increasing the duration of the receive window, the present embodiment accounts for clock drift between the docks of the transmit and receive IMDs.

Optionally, the duration of the receive window and/or the window-to-window interval may remain constant throughout operation without subsequent calibration or continuous increase. Instead, in accordance with at least one embodiment, the controllers of the transmit and receive IMDs cooperate to reestablish synchronization frequently. For example, the transmit and receive IMDs may resynchronize with one another as often as is practical, without unduly sacrificing battery life or other performance issues. By increasing the frequency of synchronization operations, clock uncertainty is reduced.

Optionally, the calibration operation may be performed based on at least one of manufacturing information and/or information received from the transmit device.

Communication Timing Resolution

FIG. 7 illustrates a timing diagram in connection with managing cooperative operation between IIIs that employ an example of a synchronous communication scheme. In the example of FIG. 7, a pair of IMDs are located in different chambers of the heart and configured to operate cooperatively to afford DDD pacing mode functionality. The IMDs operate cooperatively, and are dependent upon the occurrence of events in the other chamber. For example, when atrial and ventricular IMDs are operating in a DDD mode, the atrial IMD conveys atrial paced and sensed event information to the ventricular IMD. The ventricular IMD conveys ventricular paced and sensed event information to the atrial IMD. Based upon the paced and sensed event information from the other device, the atrial and ventricular IMDs set various flags and timers to manage local pacing. For example, the IMDs may set event interval timers that define outer time limits for related events to occur in different chambers of the heart. As one example, the ventricular IMD may utilize an AV event interval timer that is initiated when the ventricular IMD is informed (via conductive communication) that a paced or sensed event has occurred in the right atrium (e.g., a paced atrial event A or sensed atrial event P). As another example, the ventricular IMD may initiate a VV event interval timer which defines an outer limit for the delay between ventricular events. The ventricular IMD monitors the right ventricle for an intrinsic ventricular event. During standard DDD operation, when the VV and/or AV event interval timer "times out" before an intrinsic sensed event occurs in the right ventricle (e.g. intrinsic R wave), the ventricular IMD delivers a paced event (e.g., paced event V). Similarly, the atrial and ventricular IMDs operate in a reverse coordinated operation as well, such that the atrial IMD initiates event interval timers (AA event interval timer, VA event interval timer, etc.). During standard DDD operation, when the AA and/or VA event interval timers "times out" before an intrinsic sensed event occurs in the right atrium (e.g., intrinsic P wave), the atrial IMD delivers a paced event (e.g., paced event A).

In accordance with embodiments herein, when one or more of the event interval timers time out, the IMD may suspend delivery of a pacing pulse for a predetermined period of time. For example, the pacing pulse may be suspended until completion of the next successive receive window. By waiting for one more receive window, the IMD affords an opportunity to receive a communication indicating whether and when a paced or sensed event occurred in the other chamber.

With reference to FIG. 7, timelines are illustrated for atrial activity 702 (sensed or paced) and ventricular activity 708 (sensed or paced) occurring in the corresponding chambers. FIG. 7 also illustrates an atrial transmit channel 704 and a ventricular receive channel 706. Within the atrial transmit channel 704, a series of transmit windows 710-716 indicate the timing at which the atrial IMD transmits paced and/or sensed event related information. Within the ventricular receive channel 706, a series of receive windows 720-726 indicate the timing at which the ventricular IMD activates receive windows to listen for paced and/or sensed event related information.

When an atrial event P is detected at 730, the atrial IMD conductively communicates corresponding information in the next successive transmit window. The next successive transmit window represents the transmit window 711 that occurs immediately after detection at 730 of the atrial event P. The transmit window 711 includes atrial event information (denoted as "P") indicating that a sensed atrial event was detected. The ventricular IMD receives the atrial event information "P" in the receive window 721 (that overlaps the transmit window 711). In response thereto, the ventricular IMD manages delivery of pacing pulses based on event related information received from the atrial IMD. For example, the ventricular IMD sets and initiates an AV interval timer 732 in a manner similar to the operations performed in traditional DDD mode pacemakers. The ventricular IMD will generate a paced ventricular event if an intrinsic ventricular event is not sensed before the expiration of the AV interval tinier 732. In the example of FIG. 7, an intrinsic ventricular event 734 is detected before expiration of the AV interval 732, and thus the ventricular IMD need not deliver a pacing pulse. Following the sensed event at 734, the ventricular IMD restarts the VV event interval timer 733.

Next, an example is discussed in connection with an atrial sensed event P that is detected at 740. The atrial event P at 740 occurs shortly after termination of a transmit window 714. Consequently, the atrial IMD is unable to immediately convey atrial event related information in the transmit window 714. Instead, the atrial IMD waits until the next transmit window 715 before conveying atrial event information P related to the intrinsic atrial event detected at 740. In standard operation, the ventricular IMD may determine to deliver a pace pulse (ventricular event) at 742, when the VV interval timer 733 times out, if no intrinsic ventricular event was sensed following the ventricular event detected at 734. However, the ventricular IMD is unaware of the atrial event occurring at 740, at the time corresponding to 742. The ventricular IMD suspends delivery of the therapy (pacing pulse) that corresponds to expiration of the VV event interval timer 733 for at least one additional window-to-window interval following expiration of the VV event interval timer. Instead, the ventricular IMD does not receive the atrial event information P until the receive window 725. When the atrial event information P is received, the ventricular IMD, does not deliver a pace pulse at 742 (as it would if no atrial event information was received) and instead the ventricular IMD sets an AV interval 744. When the AV interval 744 expires before detection of an intrinsic ventricular event, the ventricular IMD delivers a ventricular pacing pulse at 746.

In the example of FIG. 7, the ventricular IMD sets the AV interval 744 and delays delivery of a ventricular pacing pulse (at 746) based on receipt of the atrial event activity in receive window 725. Accordingly, even when the atrial and ventricular MDs experience limitations on the level of regularity or time resolution for when conducted communication information can be conveyed, the atrial and ventricular IMDs are able to cooperate to provide DDD mode pacemaker functionality. The window-to-window interval and resultant time resolution/granularity is short enough and fine enough to not be noticeable physiologically. For example window-to-window interval would be less than the desired AV delay or the ventricular IMD will not be able to respond to the atrial IMD in a desired time period.

In the foregoing example, the IMD manages operation by initiating an event interval timer at the second/ventricular IMD. When the event interval timer expires, the second/ventricular IMD suspends delivering of pacing pulses until after a next successive receive window at the second LIMD following the expiration of the event interval timer.

The foregoing example discusses cooperation between an atrial IMD transmitting atrial event information to a ventricular IMD that performs ventricular operations based on the atrial event information. It is recognized that the same cooperative management process may apply when the ventricular IMD transmits ventricular event information to an atrial IMD that performs atrial operations based on the ventricular event information.

In the foregoing example, the ventricular IMD sets the AV interval to begin at the time when the atrial event information P is received. Optionally, the ventricular IMD may set the AV interval to begin at a different point in time or may adjust the duration of the AV interval. For example, when the atrial IMD conveys the atrial event information P, the atrial IMD may also include information indicating whether a delay has occurred between the occurrence of the atrial event and the time at which the atrial event information P is conveyed in a transmit window. Returning to the example of FIG. 7, the atrial event P is detected at 740, and a delay 750 occurs between when the atrial event information was detected and when it can be transmitted in a transmit window 715. Optionally, the atrial IMD may track the duration of the delay 750 and include the duration of the delay 750 in the communications message conveyed in the transmit window 715.

In the example of FIG. 7, the atrial IMD does not convey information in every transmit window. Instead, the atrial IMD performs selective transmission, in which atrial event activity is included in only a subset of the transmit windows. Optionally, when no information is to be conveyed, "empty" transmit windows may be omitted and the transmitter maintained in an in-active state unto it is desirable to transmit information. For example, in FIG. 7, transmit windows 710, 712-714 and 716 may be omitted entirely. During selective transmission, all of the receive windows are still turned on and off in accordance with the corresponding receive window timing scheme given that the receive IMD will not know whether a transmit IMD is transmitting during any given transmit window. During selective transmission, only a subset of the receive windows will receive conducted communication information, while a remainder of the receive windows will not receive any conducted communication information.

The ventricular IMD may analyze the message within receive window 725, to determine that an atrial event occurred at an earlier point in time based on the duration of the delay 750. The ventricular IMD may then shorten the AV interval 744 accordingly.

As yet a further option, the atrial and ventricular IMDs may utilize more than one transmit and receive window to convey information between one another regarding atrial and ventricular paced and sensed events and delays 750.

The receive amplifier of the receive IMD is not active continuously once synchronization has been achieved. Accordingly, the IMDs experience limitations on the level of regularity or time granularity/resolution for when conducted communication information can be conveyed from a transmit IMD to a receive IMD. In general, a transmit IMD may detect and record sensed or paced events at a first timing resolution determined by internal clock 109, but will only transmit the sensed or paced events through conducted communication at a second timing resolution determined by transmit window-to-window interval which is coarser than the first timing resolution.

Transmission Timing

The transmit/receive timing schemes utilized in accordance with various embodiments may be defined independent of any physiologic characteristic or behavior of the patient. For example, the transmit/receive timing scheme may be set such that transmit and receive windows have a standard window-to-window interval and window duration without regard for heartrate or other physiologic characteristics.

Alternatively, the transmit/receive timing scheme may defined to be dependent on one or more physiologic characteristics or behavior of the patient. For example, it may be desirable to manage transmit windows such that conducted communications are transmitted during a refractory period experienced by a local region of the patient. There may be various reasons for managing transmission of conducted communications only during a refractory period. For example, it may be desirable to transmit conducted communication pulses between IMDs only during the refractory period of the particular chamber(s) where the IMDs are implanted. By way of example only, limiting conducted communications pulses to a local refractory period, may, among other things, avoid unintentional stimulation of the local tissue (e.g., a chamber of the heart).

Additionally or alternatively, to avoid unintentional stimulation of local tissue by conducted communications pulses, embodiments herein may reduce the transmission amplitude and/or increase the transmission frequency of the pulses within the conducted communication. For example, the transmission amplitude and/or transmission frequency may be set in accordance with the parameters defined by the International Electrotechnical Commission (IEC) Medical Electrical Equipment—Part 1: General requirements for basic safety and essential performance (IEC-60601). It is recognized that the transmission frequency does not mean "window-to-window interval" here, but instead refers to the frequency components (e.g., Fourier transform) of the conducted communication pulses.

As another example, limiting conducted communications pulses to a refractory period avoids creation of artifacts (by the transmission circuits) that might interfere with sensing the intrinsic heart activity. Optionally, artifacts may be avoided through select analog system design.

In accordance with embodiments herein, it may be desirable to limit communication through transmit windows that coincide with the refractory period of the chamber in which the transmitting IMD is located (also referred to as the transmitting chamber). When limiting conducted communication to the refractory period of the transmitting chamber, link maintenance communication would be less frequent.

Closing

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such cams are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable medical device, comprising:
a housing configured to be implanted entirely within a first region of a patient;
electrodes;
sensing circuitry configured to detect physiologic events occurring in the first region;
a receiver amplifier coupled to the electrodes, the receiver amplifier configured to receive conducted communications signals via the electrodes; and
a controller configured to establish synchronous conducted communication with a transmit device, the controller including a receive window timing (RWT) module configured to manage an on-off cycle of the receiver amplifier based on first and second receive window timing schemes, the RWT module switching between the first and second receive window timing schemes based on a condition of the synchronous conducted communication, wherein the controller is configured to perform a calibration operation that maintains the second receive window timing scheme calibrated with a transmit window timing scheme of the transmit device, and wherein the controller performs the calibration operation by shifting a reference point defining a timing of the receive windows based on the timing difference.

2. The device of claim 1, wherein the RWT module switches between first and second receive window timing schemes that utilize first and second receive windows, respectively, having at least one of different durations or different window-to-window intervals.

3. The device of claim 1, wherein, before the synchronous conducted communication is established, the RWT module is configured to switch to the first receive window timing scheme in which a persistent active receive window is maintained.

4. The device of claim 1, wherein, after the synchronous conducted communication is established, the RWT module is configured to switch to the second receive window timing scheme that comprises a series of successive receive windows separated by in-active intervals.

5. The device of claim 4, wherein the receive windows have a duration that is substantially less than a duration of the in-active intervals separating the receive windows.

6. The device of claim 1, wherein the controller performs the calibration operation by modifying the second receive window timing scheme by shifting at least one of i) a reference point defining a timing of the receive windows, ii) a duration of the receive windows or iii) a window-to-window interval based on information received from the transmit device.

7. The device of claim 1, further comprising a pulse generator and a controller configured to analyze the physiologic events and, based, thereon manage the pulse generator to deliver a therapy in a local tissue of interest.

8. A method for providing synchronous conducted communication for an implantable medical device (IMD), the method comprising:
providing an IMD having a housing configured to be implanted entirely within a first region of a patient, the IMD including a controller, sensing circuitry, a receiver amplifier coupled to electrodes;
utilizing the electrodes to sense conducted communications from a transmitting device;
detecting physiologic events occurring in the first region;
utilizing a receiver amplifier to receive conducted communications signals via the electrodes;
establishing synchronous conducted communication with a transmit device;
managing an on-off cycle of the receiver amplifier based on first and second receive window timing schemes;
switching between the first and second receive window timing schemes based on a condition of the synchronous conducted communication; and
using the controller to perform a calibration operation that maintains the second receive window timing scheme calibrated with a transmit window timing scheme of the transmit device by shifting a reference point defining a timing of the receive windows based on the timing difference.

9. The method of claim 8, further comprising defining the second receive window timing scheme to correspond to a transmit window timing scheme utilized by the transmit device, the second receive window timing scheme and the transmit window timing scheme comprising corresponding series of successive receive and transmit windows, respectively, that are temporarily aligned with one another.

10. The method of claim 8, wherein the first receive window timing scheme is utilized before the synchronous conducted communication is established, the first receive window timing scheme maintaining a persistent active receive window.

11. The method of claim 8, further comprising switching to the second receive window timing scheme after the synchronous conducted communication is established, the second receive window timing scheme comprises a series of successive receive windows separated by in-active intervals.

12. The method of claim 8, further comprising defining the second receive window timing scheme to include receive windows having a duty cycle that represents a percentage of a period in which the receive windows are active.

13. The method of claim 8, further comprising performing a calibration operation that maintains the second receive window timing scheme calibrated with a transmit window timing scheme of the transmit device based on at least one of manufacturing information or information received from the transmit device.

14. The method of claim 8, further comprising modifying the second receive window timing scheme by increasing a duration of the receive window as a function of time relative to establishing the synchronous conducted communication.

15. A method, comprising:
configuring first and second leadless implantable medical devices (LIMDs) to operate cooperatively in a DDD pacemaker mode;
each of which includes a housing, electrodes, receive amplifier, sensing circuitry and a controller, the first and second LIMDs that configured to be implanted entirely within first and second chambers of the heart, respectively;
detecting at least one of paced or sensed events at the first LIMD;
defining a transmit window timing scheme for the first LIMD and a receive window timing scheme for the second LIMD, the transmit and receive window timing schemes including transmit and receive windows temporarily aligned with one another, the transmit and receive windows spaced apart by a window-to-window interval; when a paced or sensed event is detected at the first LIMD, transmitting, event related information in a next successive transmit window through conducted communication;
receiving the event related information at the second LIMD during a receive window overlapping the next successive transmit window;
managing delivery of pacing pulses at the second LIMD based on the event related information received from the first LIMD; and
performing selective transmission at the first LIMD, in which paced or sensed event activity is included only in a subset of the transmit windows.

16. The method of claim 15, wherein managing delivery of pacing pulses at the second LIMD based on the event related information received from the first LIMD comprises initiating an event interval timer at the second LIMD and, when the event interval timer expires, suspending delivering of pacing pulses at the second LIMD until after a next successive receive window following the expiration of the event interval timer.

17. The method of claim 15, wherein the first LIMD transmits the event related information after a delay that occurs between detection of the paced or sensed event and the next successive transmit window.

* * * * *